(12) United States Patent
Charles et al.

(10) Patent No.: US 7,934,648 B2
(45) Date of Patent: May 3, 2011

(54) SYSTEM AND METHOD FOR IDENTIFYING AND CONTROLLING OPHTHALMIC SURGICAL DEVICES AND COMPONENTS

(75) Inventors: Steven T. Charles, Memphis, TN (US); Edward G. Malk, Gilbert, AZ (US)

(73) Assignee: Alcon, Inc., Hunenberg (CH)

( * ) Notice: Subject to any disclaimer, the term of this patent is extended or adjusted under 35 U.S.C. 154(b) by 650 days.

(21) Appl. No.: 11/859,206

(22) Filed: Sep. 21, 2007

(65) Prior Publication Data

US 2008/0054073 A1 Mar. 6, 2008

Related U.S. Application Data

(63) Continuation-in-part of application No. 11/013,244, filed on Dec. 15, 2004, now Pat. No. 7,568,619.

(51) Int. Cl.
*G06F 19/00* (2006.01)
(52) U.S. Cl. ............ 235/385; 235/375; 705/28; 606/10
(58) Field of Classification Search .............. 235/385, 235/375; 705/28, 29; 606/10
See application file for complete search history.

(56) References Cited

U.S. PATENT DOCUMENTS

| | | | |
|---|---|---|---|
| 5,024,653 | A | 6/1991 | Kohnke |
| 5,085,492 | A | 2/1992 | Kelsoe et al. |
| 5,400,267 | A | 3/1995 | Denen et al. |
| 6,574,166 | B2 | 6/2003 | Niemiec |
| 6,648,223 | B2 | 11/2003 | Boukhny et al. |
| 6,801,913 | B2 | 10/2004 | Matsumura et al. |
| 6,861,954 | B2 | 3/2005 | Levin |
| 7,268,684 | B2 * | 9/2007 | Tethrake et al. ........... 340/572.1 |
| 7,568,619 | B2 | 8/2009 | Todd et al. |
| 2001/0020148 | A1 | 9/2001 | Sasse et al. |
| 2002/0017996 | A1 | 2/2002 | Niemiec |
| 2002/0032435 | A1 | 3/2002 | Levin |
| 2002/0143320 | A1 | 10/2002 | Levin |
| 2003/0127508 | A1 | 7/2003 | Jones |
| 2003/0178488 | A1 | 9/2003 | Southard |

(Continued)

FOREIGN PATENT DOCUMENTS

EP 1199046 4/2002

(Continued)

OTHER PUBLICATIONS

Lee, Y., "MCRF 355/360 Applications", AN707 Datasheet, Microchip Tech., Inc., (1999), DS007074, 8 pgs.

(Continued)

*Primary Examiner* — Ahshik Kim
(74) *Attorney, Agent, or Firm* — Armando Pastrana, Jr.

(57) ABSTRACT

A system and method for identifying a component for use with a surgical device are disclosed. A component of a surgical device includes an identifier, such as a RFID tag. Data from the RFID tag is transmitted to a RFID reader operably coupled to the device. A controller identifies the component based on the received data and determines whether the component can be used with the surgical device based on criteria, such as whether the received data is an authorized code that matches data stored in memory or whether the received data solves or satisfies an algorithm. The authorized codes are selected from a larger set of available codes. The controller can enable or disable the operation of the device with the component based on whether the criteria is satisfied and can cause the surgical device to be configured for use with the component.

10 Claims, 11 Drawing Sheets

U.S. PATENT DOCUMENTS

| | | |
|---|---|---|
| 2003/0178489 A1 | 9/2003 | Boukhny et al. |
| 2004/0220602 A1 | 11/2004 | Deng et al. |
| 2005/0118048 A1 | 6/2005 | Traxinger |
| 2006/0043177 A1* | 3/2006 | Nycz et al. .................. 235/385 |
| 2007/0094393 A1 | 4/2007 | Zwingenberger et al. |
| 2007/0216526 A1* | 9/2007 | Volpi et al. .................. 340/505 |

FOREIGN PATENT DOCUMENTS

| | | |
|---|---|---|
| EP | 1199046 A2 | 4/2002 |
| WO | 200114912 A1 | 3/2001 |
| WO | WO0114912 A1 | 3/2001 |
| WO | 2002099774 A2 | 12/2002 |
| WO | WO02099774 A2 | 12/2002 |
| WO | 2003026558 A2 | 4/2003 |
| WO | WO03026558 A2 | 4/2003 |
| WO | 2004108189 A3 | 12/2004 |
| WO | 2006036600 A1 | 4/2006 |
| WO | WO02006036600 | 4/2006 |

OTHER PUBLICATIONS

Appleby, J., "Drug makers using spy-novel strategies to thwart knockoffs.", The Seattle Times, Aug. 19, 2003, ISSN 0745-9696, 2 pgs.

ATMEL Wireless & pC, "Electronic Immobilizers for the Automotive Industry", Jun. 2003, Link: http://www.atmel.com/dyn/resources/prod_documents/doc3a78163c4000a.pdf, 13 pgs.

Pharmpack Europe, [Special Compliance] "Smart Packages May Help Control Presecriptions", Nov. 2005, vol. 5, p. 30.

Pharmpack Europe, [Special Compliance] "Labeling: Fitting Everything In", Nov. 2002, vol. 5, p. 31.

RU27481U1; ABSTRACT only; Device for the [Vitreoretinalnoy] Surgery [FAMPAT Machine Translation]; Oct. 2, 2003.

SU1364333; ABSTRACT only; "Method of Closed Vitrectomy" [FAMPAT Machine Translation]; Jan. 7, 1988.

RU2212867C2; ABSTRACT only; "Method for Treating the Cases of Intraocular Tumors"; Sep. 27, 2003; espacenet database.

* cited by examiner

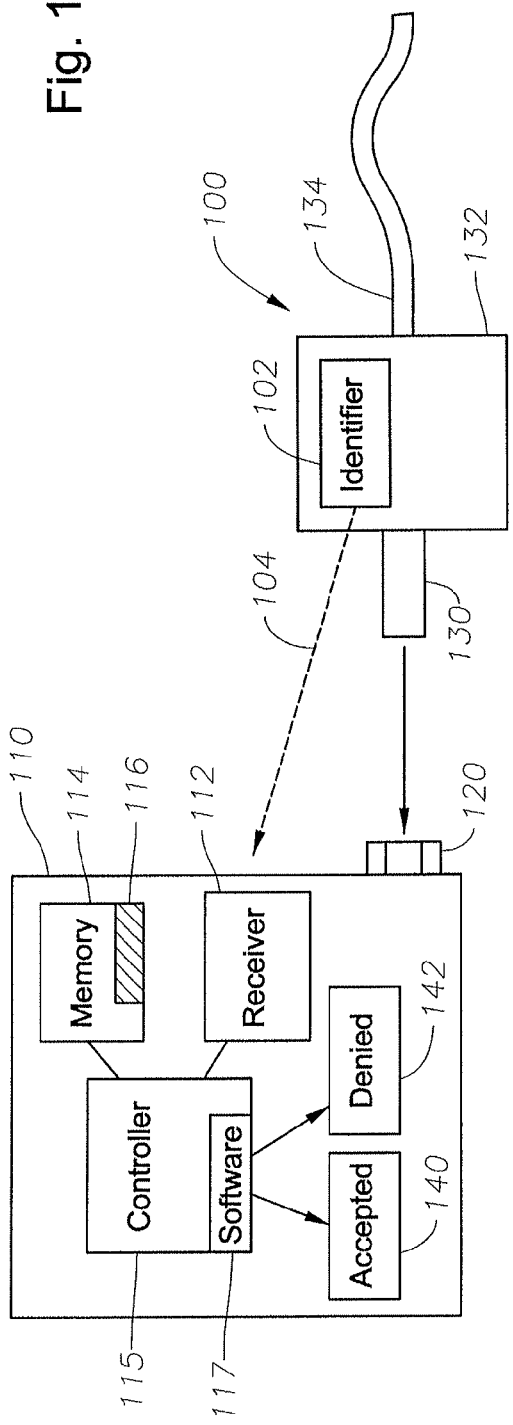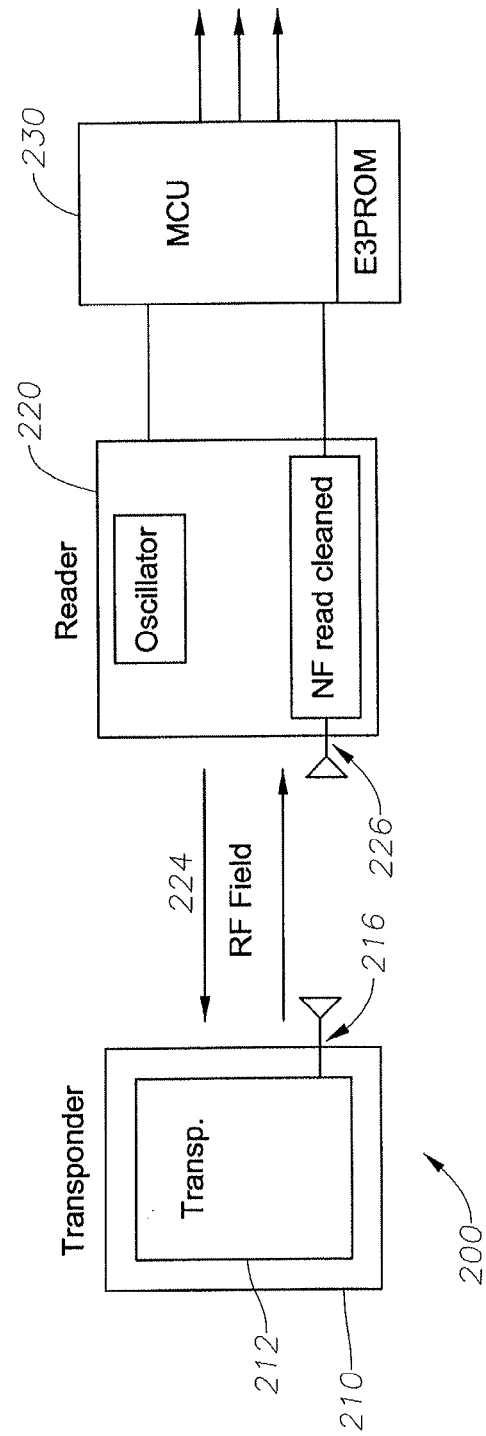

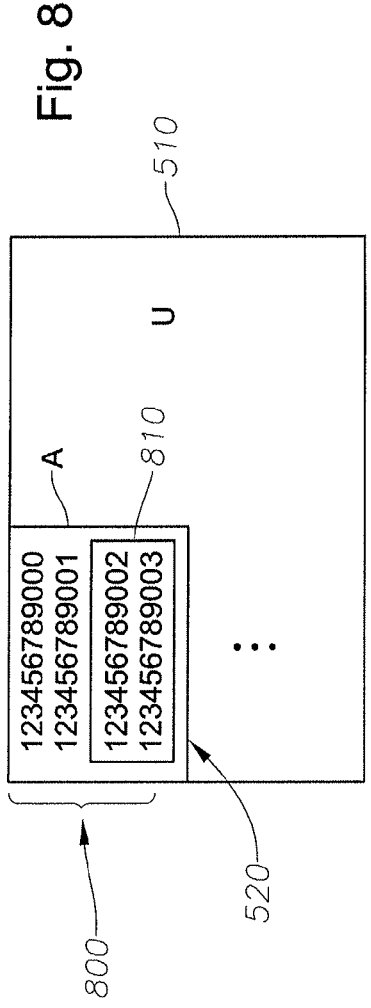
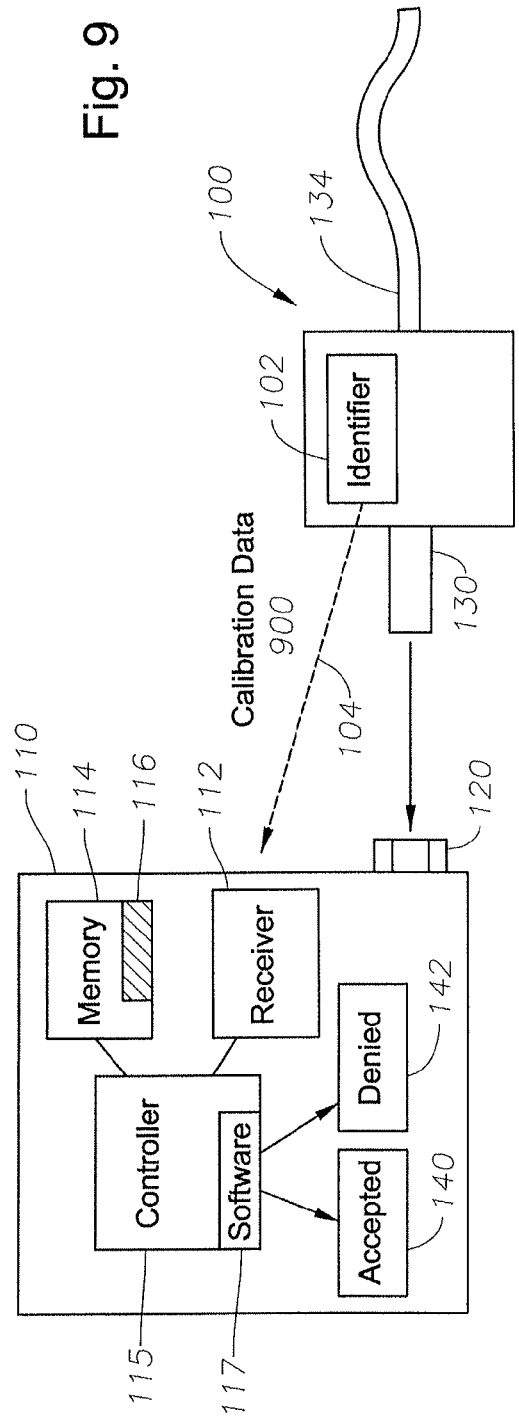

SYSTEM AND METHOD FOR IDENTIFYING AND CONTROLLING OPHTHALMIC SURGICAL DEVICES AND COMPONENTS

RELATED APPLICATION

The present application is a continuation-in-part (CIP) of a U.S. patent application entitled "System and Method for Identifying and Controlling Ophthalmic Surgical Devices and Components," filed on December 15, 2004, and having a Ser. No. 11/013244, and issued as U.S. Pat. No. 7,568,619, which is herein incorporated by reference in its entirety.

TECHNICAL FIELD OF THE INVENTION

The present invention relates to surgical devices, and, more particularly, to the use of electronic identifiers on components of surgical devices that can be used to transmit and receive data related to the components and use thereof with the surgical device.

BACKGROUND OF THE INVENTION

Various surgical systems and devices are operated using components that are discarded or replaced for various reasons. For example, components may be discarded because they are contaminated or because they have exceeded a certain useful life. Thus, unlike permanent surgical equipment, some components are used one time, or a limited number of times, and then must be replaced for safety and/or other considerations. Determinations regarding whether a particular component is suited for a particular surgical device are typically made by a technician or surgeon, for example, based on whether the component fits within or attaches to the surgical device, and the operating specifications of the component and the device. Other aspects related to the use of particular components are also left to user discretion, including activation of the surgical device, calibration of the device to operate with a particular component, and the manner in which the device operates with a particular component. Thus, the selection of components and operation of the device are often subject to user discretion.

Further, various surgical devices and systems are operated using various components at different points during a procedure. For example, different handpieces, illumination devices and/or other manual instruments may be needed within a surgical field at different times and each may require configuring the surgical system for use with that instrument. As a result, a surgeon typically will require an assistant, such as a scrub nurse or technician, to select the instrument or otherwise configure the surgical system for use with the instrument. This will distract the assistant from performing other duties in furtherance of the surgical procedure and thereby interfere with other preparations and/or lengthen the time required to complete the procedure.

Known systems and techniques for matching surgical devices and components, however, can be prone to error and require additional time and effort to ensure that the correct component is attached to the correct surgical device. Further, there are problems associated with third parties manufacturing components for replacement of original surgical components. Third-party replacement components can have a number of shortcomings. For example, they may be lower quality components compared to components from original manufacturers. They may also not function as intended and be less reliable than original manufacturer components, thus causing system operation and safety concerns. Additionally, manufacturers of original equipment experience increased competition from third parties who manufacture and sell components that are intended to replace original equipment.

There have been attempts to address some of these concerns, but only with specific types of medical equipment and with limited effectiveness. One approach has been to utilize Radio Frequency Identification (RFID) systems. RFID systems are well known and use electronic tags or transponders for storing data. Some RFID systems use passive tags that are activated when they are brought into proximity to a transmitted radio signal, whereas other RFID systems use active tags that include an independent power source to operate independently.

RFID tags (devices) have been used with certain types of medical equipment but, to the Applicants' knowledge, not with ophthalmic surgical devices. For example, one known system uses RFID devices in connection with disposable optical fiber components of a medical laser system in which fiber optic strands are inserted into the body. The strands are exposed to body fluids and must be disposed of after every use, or thoroughly disinfected. Other known systems use RFID devices with catheters that are inserted into the vascular system and directed into the heart. These known systems, however, use RFID devices for particular surgical devices and provide limited functionality for identifying replacement components that are not original equipment components.

Another known system is used to track surgical implements. A sensor system records the time each surgical implement is checked-out/used. When the surgical implement has been used, it is placed on or near the sensor and check-in information is recorded. This system is used to track surgical implements during a procedure and to ensure that no medical implements are inadvertently left behind inside a patient.

Thus, known systems and techniques for identifying surgical equipment, in particular, ophthalmic surgical equipment, can be improved. To the Applicants' knowledge, RFID technology has yet to be effectively applied to ophthalmic surgery systems and components. Further, the use of RFID tags in other medical devices is typically limited to basic identification functions and enabling or disabling equipment. Thus, known systems do not provide other, more useful data concerning the component and its functionality, which can assist surgeons when using the equipment. Such information may include, for example, calibration data and data related to the history of the component. Accordingly, the manner in which components of ophthalmic and other surgical systems and equipment are utilized can be improved, including the integration of data transmission devices, such as RFID devices, to perform identification and other functions that are not provided by known systems, and by providing the ability to provide additional information relating to the component to surgeons.

BRIEF SUMMARY OF THE INVENTION

According to one embodiment of the present invention, a system for identifying a component that is used with a surgical device or system includes a radio frequency identification (RFID) tag that is part of the component, a receiver, a memory for storing criteria and a controller, which are included in the surgical device. Data from the RFID tag is transmitted to the receiver in the surgical device. The controller identifies the component and determines whether the component corresponding to the received data can be used with the surgical device based on whether the received data satisfies the criteria stored in memory. If so, the controller is operable to cause the surgical device to be configured for use with the component without operator action.

In a further embodiment, a system for identifying a component that is used with a surgical device or system, such as an ophthalmic surgical device, includes a radio frequency identification (RFID) tag that is part of the component, a receiver, a memory for storing criteria and a controller, which are included in the surgical device. Data from the RFID tag is transmitted to the receiver in the ophthalmic surgical device, and the controller determines whether the component corresponding to the received data can be used with the ophthalmic surgical device by determining whether the received data is an authorized code that satisfies the criteria stored in the memory. The authorized codes are selected from a larger set of codes, including both authorized and unauthorized codes.

In a further alternative embodiment, a system for identifying a component that is used with an ophthalmic surgical device includes a radio frequency identification (RFID) tag in the component, a receiver, a memory for storing criteria and a controller in the surgical device. Unencrypted data from the RFID tag is transmitted to the receiver. The controller determines whether the component corresponding to the received unencrypted data can be used with the ophthalmic surgical device based on whether the received unencrypted data is an authorized code that satisfies the criteria in memory. Authorized codes are selected from a larger set of available codes, including both authorized and unauthorized codes.

Yet a further alternative embodiment is a method of identifying a component that can be used with an ophthalmic surgical device. The method includes establishing criteria and storing criteria in a memory of the ophthalmic surgical device and transmitting data from an identifier in the component to a receiver in the ophthalmic surgical device. Data received from the identifier is processed to determine whether the received data is an authorized code that satisfies the criteria stored in the memory to determine whether the component corresponding to the received data can be used with the ophthalmic surgical device.

In various embodiments, the criteria can be authorized data, e.g., authorized numbers, that are stored in the memory. The data that is received from the identifier is compared to the authorized data to determine whether the component can be used with the ophthalmic surgical device. For example, the device can be enabled if the received data matches the authorized data criteria. Further, the criteria can be an algorithm, a formula or other pre-defined criteria (generally "algorithm"). The algorithm is applied to the data that is received from the identifier to determine whether the component can be used with the ophthalmic surgical device based on, for example, whether the received data solves or satisfies the algorithm or formula.

In various embodiments, different surgical devices and components can be utilized. For example, the surgical device can be an ophthalmic surgical device, such as a laser or laser console, and the component can be a laser probe that is attached to the device. In other embodiments, the ophthalmic surgical device can be a phacoemulsification system or a vitreoretinal surgical system, and the component can be a vitrectomy probe, a phacoemulsification handpiece, a pneumatically or electrically powered scissors, or an endoilluminator probe that is attached to the surgical system.

Further, in embodiments using RFID components, the receiver can be a RFID reader, and the identifier can be a RFID tag, and the data in the RFID tag or identifier may be unencrypted.

One manner of selecting authorized codes that satisfy the criteria is to select authorized codes from a larger set of available codes, which includes both authorized and unauthorized codes. For example, in one embodiment, the number of authorized codes is at least three orders of magnitude greater than a number of available codes; e.g., one billion authorized codes are selected from one trillion codes. In one embodiment, the identifier data includes 14 bytes. Two bytes are used to identify the type of component, and 12 bytes are used to identify one trillion codes.

System embodiments can be configured to enable or disable a surgical device or system. If the data received from the identifier satisfies the criteria, then the device can be enabled. The device can also be conditionally enabled based on, for example, whether the component has been used before, or based on an amount of time that has passed since a first or prior use of the component. A certain number of repeat uses of a component may be allowed, but the device can be disabled after a certain number of uses or after a certain amount of time. Other safety precautions can also be implemented, such as generating a message to a surgeon that the component has been previously used. Further, data can be written back to the component identifier for future reference. The data may include a date of usage, a number of uses of the component, a duration of use of the component, or a power setting of the component. The device can also be enabled based on geographic restrictions.

In various embodiments, the identifier can also include calibration data that indicates how the ophthalmic surgical device should be configured to work with a particular component. Further, identification data and/or calibration data can be used for various purposes. For example, a user interface that is presented on a display screen can be generated based on the particular component that is utilized. Data can also be used to enable operating parameters that are compatible with the identified component and to disable operating parameters that are incompatible with the identified component. The data can be used to implement safety procedures, for example, limiting the value of power, exposure range and other operating parameters, and checking whether a safety component, such as a filter that is associated with the identified component, is present.

BRIEF DESCRIPTION OF THE DRAWINGS

A more complete understanding of embodiments and the advantages thereof may be acquired by referring to the following description, taken in conjunction with the accompanying drawings, in which like reference numbers indicate like features and wherein:

FIG. 1 is a block diagram of a system according to one embodiment that includes an ophthalmic surgical device and a component that is used with the device and that includes an identifier;

FIG. 2 illustrates an exemplary RFID system that can be used with ophthalmic surgical devices and components thereof;

FIG. 8 illustrates how unencrypted authorized codes can be serialized to define groups or lots of components that can be used with a surgical device;

FIG. 9 illustrates an alternative embodiment in which data transmitted from the identifier in the component includes information for calibrating an ophthalmic surgical device;

DETAILED DESCRIPTION OF ILLUSTRATED EMBODIMENTS

In the following description, reference is made to the accompanying drawings, which form a part hereof, and which show by way of illustration specific embodiments. It is to be understood that structural changes may be made without departing from the scope of the embodiments.

System and method embodiments provide for electronic identifiers to be integrated into surgical equipment, such as ophthalmic surgical equipment. The electronic identifiers can perform various functions, including identifying a component or adaptation that can be used with an ophthalmic surgical device, selectively enabling and disabling equipment that is used with components, identifying unauthorized components, such as components that are not compatible with a device and components from third party manufacturers, providing calibration data, and providing for read/write applications between an ophthalmic surgical device and a component used with the device. Thus, embodiments allow for more accurate determinations whether certain components or adaptations are compatible with certain surgical devices. Further, embodiments provide for enhanced functionality, thus improving the effectiveness and safety of ophthalmic surgical procedures by ensuring that only suitable components are used with the device. Additionally, embodiments allow original surgical equipment manufactures to retain tighter control over their inventory and the use of original and valid components, thereby providing improved performance, regulatory compliance and tracking of products. These and other aspects of embodiments are discussed in further detail below.

Figure 1A:
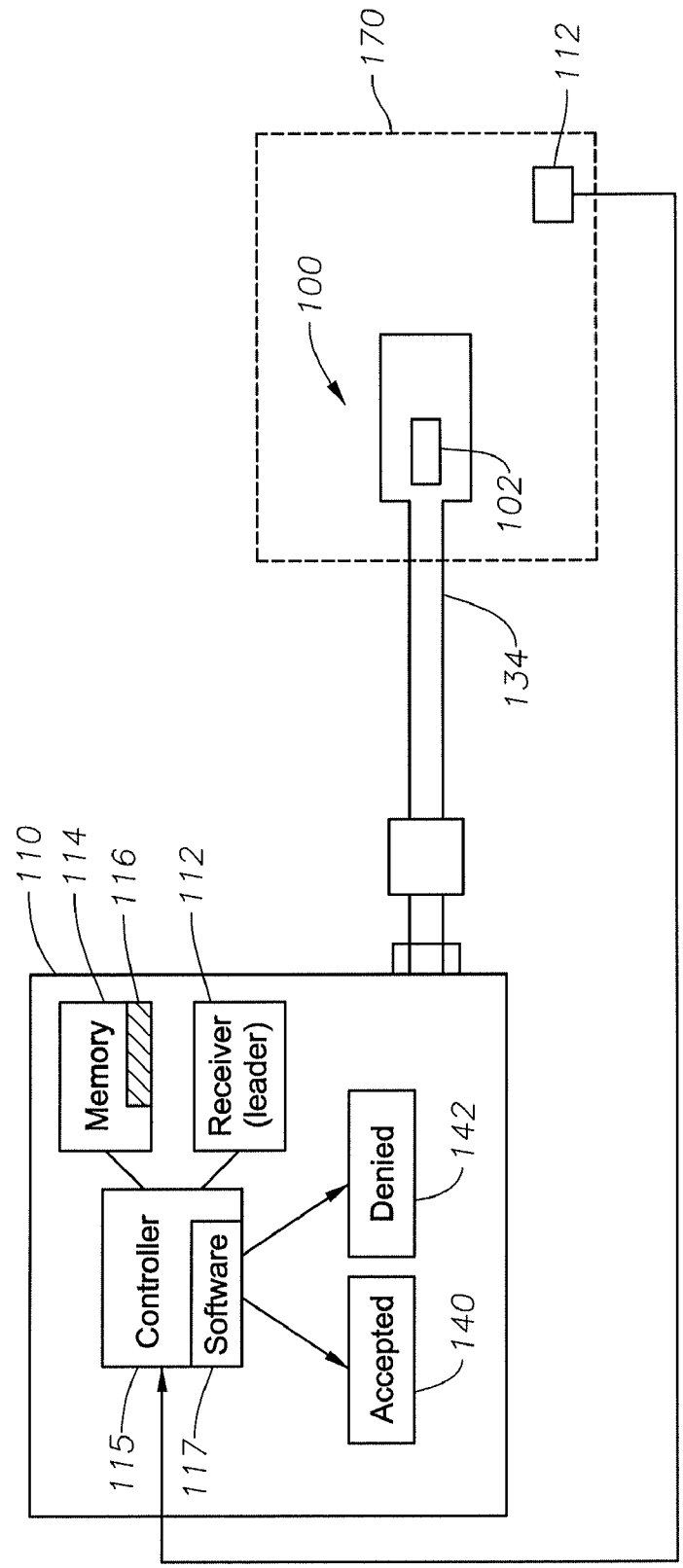
FIG. 1A is a block diagram of an embodiment of the present invention implemented as part of a surgical system wherein a component is identified and a surgical console configured for use with the component when the component enters a surgical workspace.

Referring to FIG. 1, according to one embodiment, a system 1 includes an ophthalmic surgical device 110 and an ophthalmic surgical component or adaptation 100 that is attached to and used with the surgical device 110. The component 100 is connected to the surgical device 110 via an input port or connector 120 of the surgical device 110 and a connector 130 of the component 100. Wireless communications between certain surgical devices and components may also be utilized.

An identifier 102 is integrated into the component 100. The identifier 102 transmits data 104 to a receiver 112 of the surgical device 110. The identifier data 104 can be used to determine whether the component 100 is an authorized component that can be used with the surgical device 110 or can simply identify the component 100. More particularly, each component 100 can be programmed with particular data 104. The surgical device 110 includes a memory 114 that stores criteria 116, such as a set of authorized codes or data, or an algorithm, formula or other pre-defined criteria (generally, "algorithm"). The memory can be a memory element that is readily accessible or a memory element that is integrated within other system components, depending on security requirements.

A controller 115, such as a processor or micro controller (generally "controller"), is programmed with software and/or hardware 117 that processes the data 104 received from the identifier 102 and the criteria 116 stored in memory 114 to determine whether the component 100 should be accepted 140 or denied 142 and whether the surgical device 110 should be enabled or disabled.

In one embodiment, the surgical device 110 is an ophthalmic laser console and the component 100 is an optical probe. As generally illustrated in FIG. 1, an optical probe 100 includes a connector 130 for attachment to the console 110 via a connector 120 of the console 110, a housing 132, and an optical fiber 134. Light generated by the console 110 is provided to the probe 100, which is manipulated by a surgeon so that the light is delivered by the optical fiber 134 to the surgical site.

One exemplary laser console 110 and optical probe 100 combination that can be used with embodiments of the invention include the Eyelite laser system, part no. 806550001, available from Alcon Laboratories Inc., 6201 South Freeway, Fort Worth, Tex. 76134. Other laser consoles from Alcon Laboratories may also be utilized. Exemplary components for connection to a laser console 110, such as the Eyelite laser system, include fiber optic probe connectors that are used with the LIO-AT Headset system, such as connector part nos. 8065741019, 8065501003, and 8065501101; a fiber that is provided with the LIO-AT Headset system, such as part no. 8065741106; and various Endo Probe fibers, such as part nos. 8065010719, 8065010503, 8065010219, 8065010203, 8065010739, 8065010419, 8065010319, 8065010403, and 8065010404, which are also available from Alcon Laboratories, Inc.

Persons skilled in the art will appreciate that embodiments can be used with other ophthalmic surgical devices 110 and components or adaptations 100. As a further example, the control console 110 may be a vitrectomy console, and the components 100 that are attached to the console can include, but are not limited to, a vitrectomy probe, a pneumatically or electrically powered scissors, an endoilluminator probe and a retinal surgery component. An exemplary vitrectomy console 110 is part no. 8065741008, available from Alcon Laboratories, Inc. Exemplary components that can be attached to the vitrectomy console include vitrectomy probe part no. 8065741018, pneumatic scissors part no. 8065808101, and endoilluminator part no. 8065740264, all of which are also available from Alcon Laboratories, Inc. For purposes of explanation, not limitation, this specification refers to an ophthalmic surgical device 110 that is a laser console and a component or adaptation 100 that is an optical probe that is connected to the console 110 and used to deliver laser energy to a surgical site. However, persons skilled in the art will appreciate that a vitrectomy console and various related components can also be utilized.

One embodiment of the present invention implemented as part of a surgical control console 110 (e.g., a vitrectomy, phacoemulsification or other surgical console 110) can comprise an identifier 102 in a portion of a component 100 that is intended to enter a surgical workspace 170. In such an embodiment, illustrated in FIG. 1A, the identifier 102 can transmit data 104 that is received and processed by the surgical console 110 via a receiver 112 located within or near the surgical workspace 170. For example, the surgical workspace 170 can comprise a sterile surgical area and the receiver 112 can be located under a drape near the eye (or other sterile surgical area) to sense and identify component 100 when it is brought into the surgical workspace 170. For example, component 100 can be a handpiece brought into the surgical area by the surgeon's hand.

Once component 100 is detected and identified, controller 115, in a similar manner as discussed elsewhere herein, is operable to cause the identified component 100 to be selected at surgical console 110 such that surgical console 110 is configured to operate component 100. This eliminates the need for a surgical assistant to manually select the component 100 at surgical console 110 via, for example, a touch screen or voice recognition. Surgical console 110 can also be operable to confirm, for example, via voice confirmation, the selection of component 100 so that the surgeon is aware of the console/component mode in use. Further, the surgeon, as a safety measure, can be required to place the surgical system in, for example, a standby mode (such as by returning a surgical footpedal to a start position), before the component 100 is enabled for use. The component 100 can thus be automatically selected, and surgical console 110 automatically configured to use component 100, as required by the surgeon and without need of a surgical assistant. The surgical assistant will then be freed to perform other functions in support of the surgical procedure. Receiver 112 and identifier 102 can be RFID components as described further below.

According to one embodiment, the receiver 112 in the console 110 and the identifier 102 in the probe 100 are Radio Frequency Identification (RFID) components. One exemplary RFID system that can be used with various embodiments includes part no. MCRF355, available from Microchip Technology, Inc., as described in Specification Sheet AN707, MCRF 355/360 Applications, the contents of which are incorporated herein by reference as though set forth in full.

FIG. 2 generally illustrates one exemplary RFID system 200 that can be used with embodiments of this invention. A RFID tag 210 typically includes an Integrated Circuit (IC), such as an Application Specific Integrated Circuit (ASIC), that includes a memory for storing data. A transponder 212 is activated by Radio Frequency (RF) instruction or signal 224 from the reader 220, which is sent through the reader antenna 226, for example, in response to a micro-controller unit 230, and received by an antenna 216 of the transponder 212 to wirelessly write data to or read data from the memory of the transponder 212.

For example, when the RFID tag 210 is to be read, the reader 220 sends out a 134.2 KHz power pulse to the antenna 226 lasting approximately 50 ms. The magnetic field generated is collected by the antenna 216 in the tag 210 that is tuned to the same frequency. This received AC energy is rectified and stored in a small capacitor within the transponder 212. After completion of the power pulse, the transponder 212 transmits back its data, using the energy stored in the capacitor as a power source. In this exemplary implementation, a total of 128 bits are transmitted (including error detection information) over a period of 20 ms. This data is received by the antenna 226 and decoded by the reader unit 220 and controller 230. The capacitor is discharged after the data has been transmitted, and the transponder 212 is reset and ready for the next read cycle.

The RFID configuration described above is "passive" since the transponder is powered by power stored in a capacitor that is generated by the RF signal from the reader. Thus, a passive RFID identifier is normally inactive and does not have an independent power source. The RFID system may also be active if a separate power source or battery is provided. Further details concerning the manner in which RFID systems operate is well known in the art and, therefore, is not discussed in further detail in this specification. For purposes of explanation, not limitation, this specification refers to RFID components that are used for transmitting data between a console 110 and a probe 100. However, persons skilled in the art will recognize that other transmitter, receiver and transceiver components can also be utilized.

When RFID components are applied to embodiments to provide communications between a surgical console 110 and probe components 100, the identifier 102 in the probe component 100 is a RFID tag or transponder 210, and the receiver 112 of the console 110 is a RFID reader 220. The RFID tag or identifier 102 includes the identification and, if applicable, other data relating to the component. The controller 115 includes software and/or hardware 117 to implement the criteria 116 to determine whether data 104 sent by the RFID tag 102 of the probe 100 and received by the RFID reader 112 of the console 110 indicates that the probe 100 can be used with the console 110.

For example, the console 110 can be enabled if the data 104 is accepted 140, or disabled if the data 104 is denied 142. The console 110 can also be conditionally enabled. For example, the console 110 may operate normally or, alternatively, in a safe mode at lower power levels. The console 110 can also be conditionally enabled when, for example, the same probe 100 has been used too many times before. The controller 115 can configure the console 110 to operate in a different manner in view of safety and other considerations since the probe 100 may not function as intended due to, for example, incompatible specifications, excessive use and wear, or expiration of the probe 100.

Figure 3:
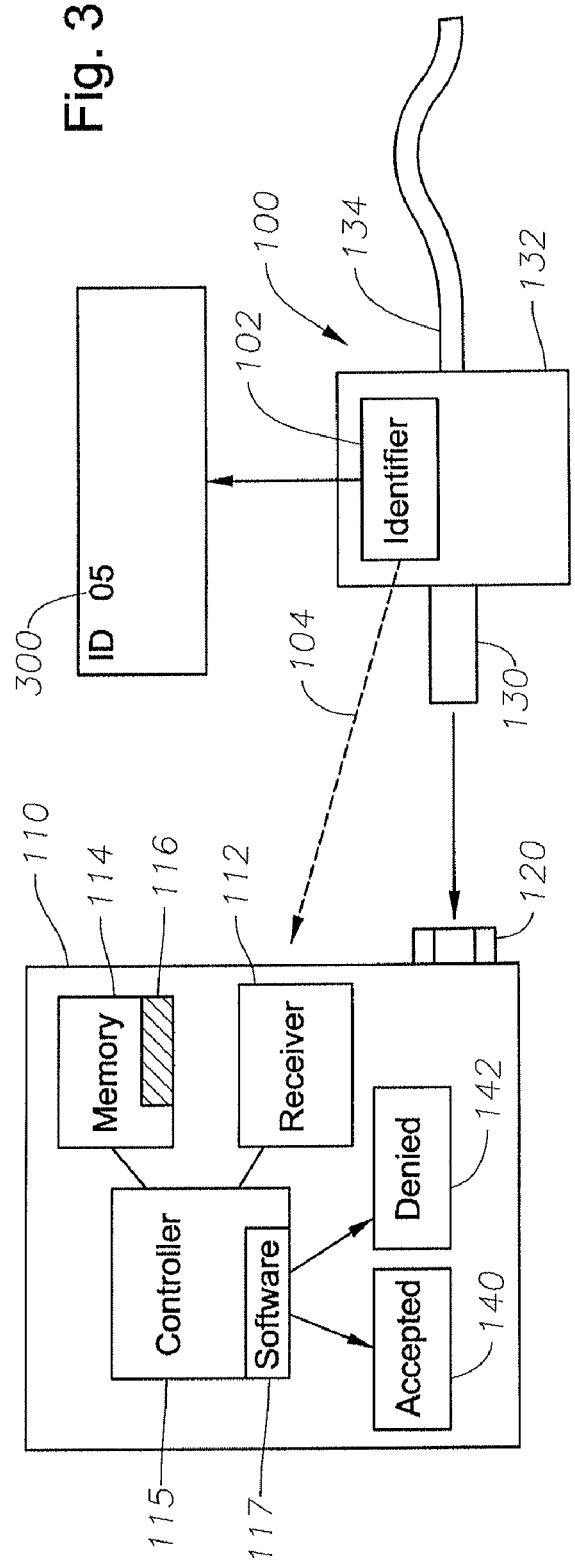
FIG. 3 illustrates an identifier of a component according to one embodiment.

More particularly, referring to FIG. 3, according to one embodiment, data 104 transmitted by the RFID tag 102 includes a two byte code or identification data 300. The two byte code can represent numbers 00-99 to identify 100 different types of probes 100. The controller 115 can apply the criteria 116 to the data 300 stored in memory 114 to determine whether the data 104 is accepted 140 or denied 142 and whether the console 110 should be enabled or disabled.

Figure 4:
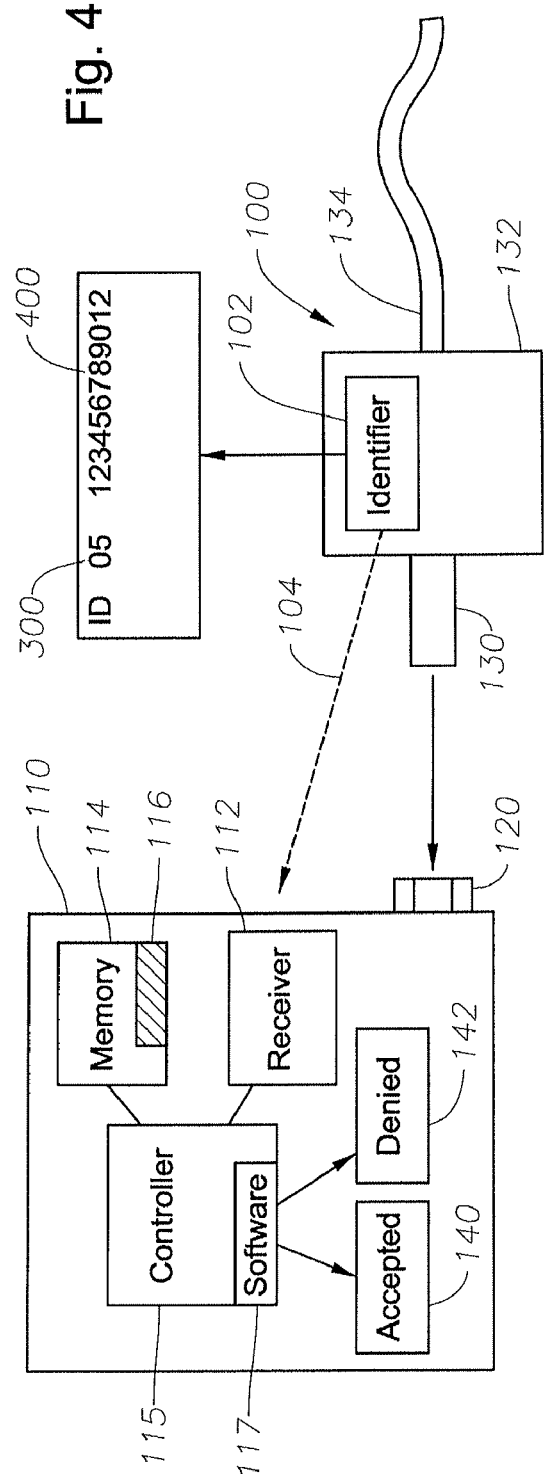
FIG. 4 illustrates an identifier and an unencrypted security code or number of a component according to one embodiment.
Figure 5:
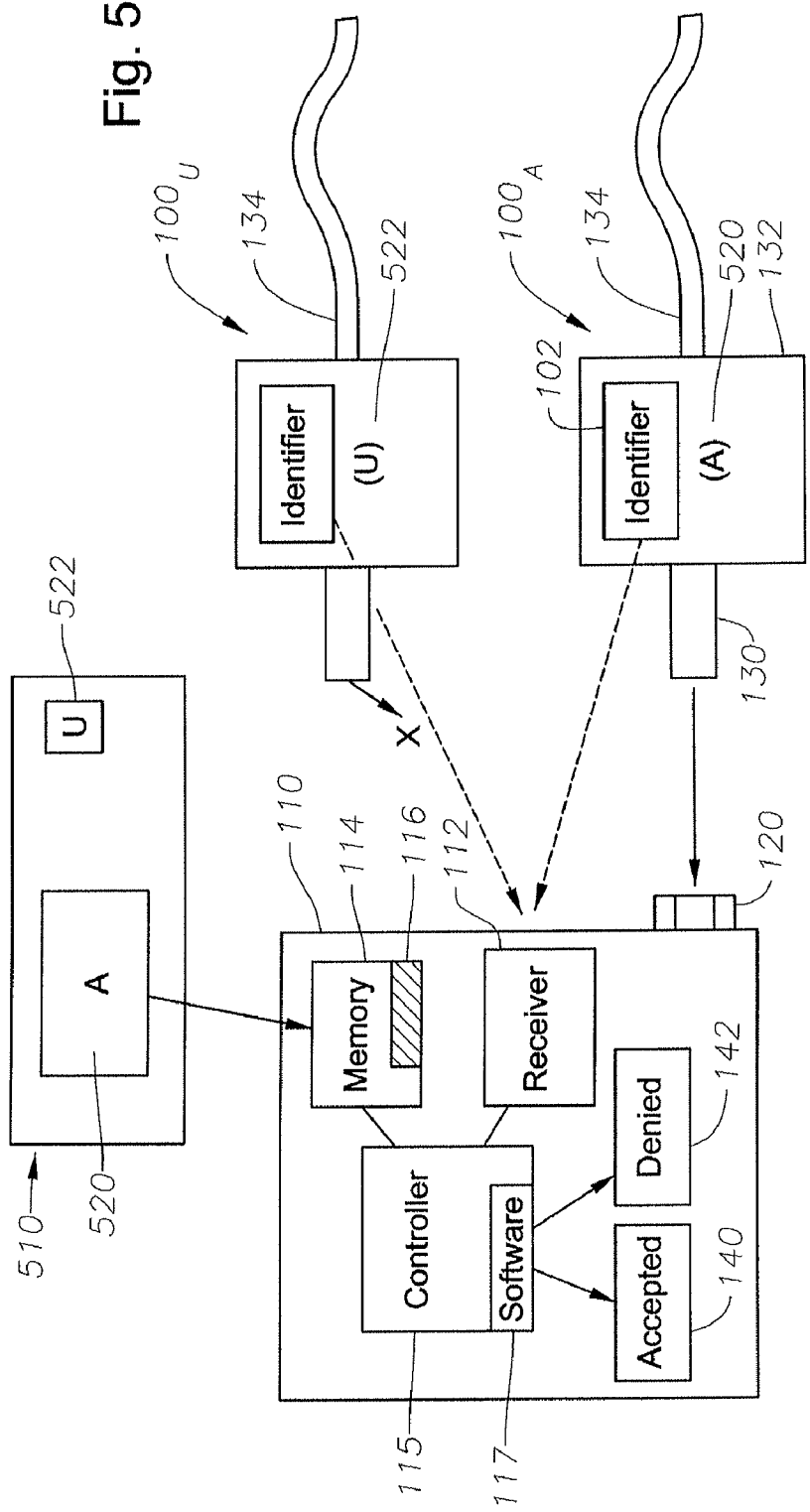
FIG. 5 illustrates a system according to one embodiment in which authorized unencrypted identifier codes or numbers are selected from a larger set of available codes or numbers.

Referring to FIGS. 4 and 5, according to another embodiment, the data 104 transmitted by the RFID tag or identifier 102 is a 14 byte code. The 14 bytes are divided into two groups: two bytes of identification data 300 (as discussed above with respect to FIG. 3) and 12 bytes of security data 400. The security data 400 is selected from a larger set of potential security codes 510. A subset of the potential codes 510 is selected as authorized codes 520. Persons skilled in the art will appreciate that the security data 400 and authorized codes 510 can be numeric, alpha-numeric, or another representation. Additionally, they may use different number systems, such as binary, hexadecimal or decimal. Thus, "code" is not intended to be limited to a particular type of code. Further, in some embodiments, no code may be used.

The 12 bytes of the security code 400 provide one trillion possible security codes 510, i.e., numbers 000000000000 to 999999999999. This is represented in FIG. 5 as (A+U) 510, or authorized codes (A) 520+unauthorized codes (U) 522. Certain codes are selected from these one trillion potential codes 510 as authorized codes 520. In one embodiment, the set of potential security codes 510 includes one trillion codes, and one billion codes are selected as authorized codes (A) 520. The remaining codes are unauthorized codes (U) 522. Thus, in this embodiment, the number of potential codes 510 is at least three orders of magnitude greater than the number of authorized codes (A) 520. The one billion authorized codes (A) 520 can be selected using, for example, a random number generator or another suitable algorithm or selection criteria. The selection algorithm can have different levels of complexity is for different security levels and applications.

Identifiers 102 of each probe 100 from an original manufacturer can be programmed with one of the authorized codes (A) 520. The authorized codes (A) 520 satisfy the criteria 116 stored in memory 114. For example, if the criteria 116 comprise a set of authorized data that is stored in memory 114, the authorized data 116 may be the same as or match the authorized codes (A) 520, whereas the unauthorized codes (U) 522 would not match the authorized data criteria 116. As a further example, if the criteria 116 is an algorithm, then the authorized codes (A) 520 would satisfy or solve the algorithm, whereas the unauthorized codes (U) 522 would not solve or satisfy the algorithm criteria 116.

In an embodiment in which the criterion 116 is an algorithm, it is not necessary to store a set of authorized data in memory since the algorithm is applied to security data received from the identifier. This may be beneficial when memory capabilities and security are concerns. An algorithm can be programmed with varying levels of complexity to provide different levels of security. Further, an algorithm can be stored in memory of various system components so that the criteria can be difficult to determine. Accordingly, although FIG. 5 shows the authorized codes (A) 520 being stored to memory, this is representative of the authorized codes that satisfy or solve the algorithm, since it is not necessary to store the authorized codes in memory when using an algorithm.

Thus, the security data 400 stored in the RFID tag 102 of a probe 100 may or may not satisfy the criteria 116 stored in memory 114. In the event that the probe 100 is from an original manufacturer, the identifier 102 includes an authorized code (A) 520 that would satisfy the criteria 116. However, if the probe 100 is from a third party manufacturer, the identifier 102 may or may not include an authorized code (A) 520, as discussed in further detail below.

When a probe 100 is connected to the laser console 110, or when the probe 100 enters the surgical workspace 170 (for an embodiment wherein the RFID tag 102 is located in a component intended to be identified when entering a surgical workspace 170), the RFID tag 102 transmits the 2-digit identification code 300 and the 12-digit security code 400 to the RFID reader 112. The controller 115 determines whether the 2-digit identification code and/or the 12-digit security code 400 satisfy the criteria 116 stored in memory 114 of the console 110.

If, for example, the security code 400 satisfies the criteria 116, e.g., the security code 400 matches one of the one billion authorized codes (A) 520 stored in memory 116 or satisfies or solves an algorithm, then the console 110 can be enabled by the controller 115. In contrast, the console 100 can be disabled if the code 400 does not satisfy the criteria 116 and is one of the unauthorized (U) codes 510 or an unrecognized code. Thus, as shown in FIG. 5, the probe 100A includes authorized security data 400 and, therefore, can be used with the console 110, whereas the probe 100U cannot be used with the console 110 because it is programmed with an unauthorized code (U) 522, which does not satisfy the criteria 116.

Selecting authorized codes 520 from a sufficiently large set of possible codes 510 facilitates the ability of manufactures of original probe components 100 to ensure that only original components are utilized and that replacement components from third parties are likely to block operation of the console 110. This can be accomplished even without having to utilize encryption/decryption techniques and the additional encryption/decryption hardware and software, which can increase the costs and complexities of the system. Rather, the authorized codes (A) 520 can remain unencrypted, and sufficient security is provided by the fact that the subset of authorized codes (A) 520 is selected from a sufficiently large pool of potential codes (A+U) 510 so that the probability of a third party manufacturer selecting an authorized code 520 is sufficiently low. This can ensure that components from original manufactures are the primary components that enable the console 110, which may be particularly useful considering that some third party replacement components may not meet the original component specifications and may not function as well as components from original manufactures and, therefore, present safety and liability concerns when using the console 110. Of course, persons skilled in the art will appreciate that encryption and decryption components can be utilized to provide additional security.

For example, in the embodiment in which one billion different authorized codes (A) 520 are selected from one trillion potential codes (A+U) 510, the total number of possible codes 510 is at least three orders of magnitude greater than the selected number of authorized codes. In this embodiment, there would only be a $1/1000$ probability that the third party replacement component would satisfy the criteria 116 and be accepted by controller 115 of the console 100, thus enabling the console 100 to work with the component. The probability can be increased or decreased by adjusting the number of bytes in the security code 400, the number of authorized codes 520, and/or the number of unauthorized codes 522. Accordingly, the example involving one billion authorized codes (A) 520 and one trillion total potential codes (A+U) 510 is not intended to be limiting.

It is possible for a third party to repeatedly use a probe 100 that has been accepted by the console 100 since the accepted probe 100 includes an authorized code (A) 520. A third party manufacturer may also purchase a small number of original equipment probes and then use the security data 400 from those probes to program other replacement components. However, embodiments can be configured to disable the console 100 after a certain number of uses or occurrences of a particular security code 400 or after a pre-determined amount of time following the first instance of a number. For example, when the criteria 116 is an algorithm, the algorithm 116 can be configured or programmed to allow a certain number of uses or a use within a period of time.

Figure 6:
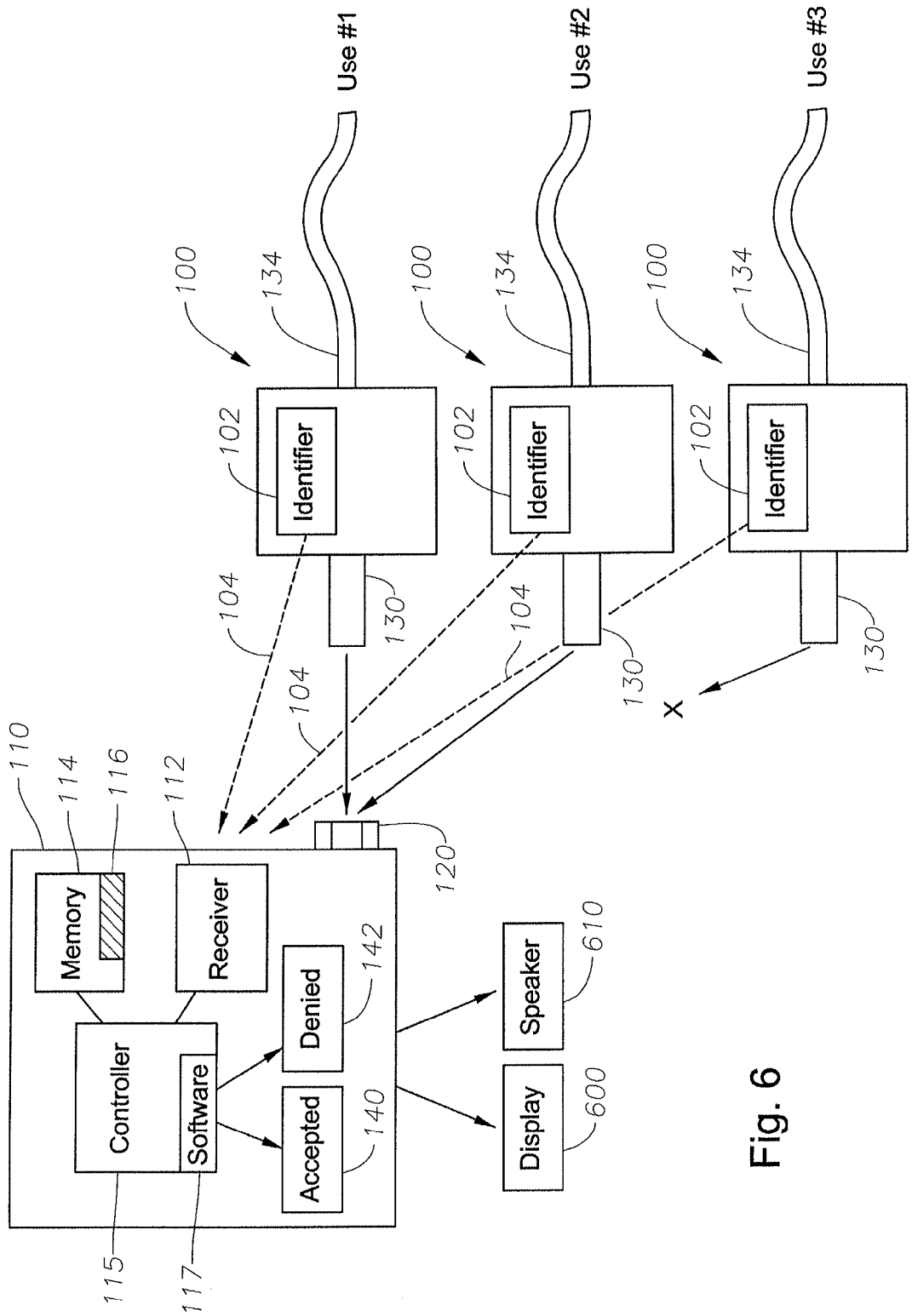
FIG. 6 illustrates an alternative embodiment in which an ophthalmic surgical device is disabled or conditionally enabled depending on the number of uses of a component.

For example, referring to FIG. 6, when the RFID tag 102 of an original probe 100 transmits the security code 400 to the RFID reader 112, the security data 400 matches, satisfies or solves the criteria 116. Thus, the console 110 will be enabled to operate with that component 100. There may be attempts to re-use the same probe since it has an authorized code (A) 520 that satisfies the criteria 116. Multiple uses of a probe 100 may be suitable in some instances; however, in order to ensure that proper regulatory and safety guidelines are followed, it is advisable in some instances that each authorized probe 100 be used only a single time. To address these concerns, the controller 115 can be programmed to disable the console 110 after a pre-determined number of uses of the same probe 100 or after a pre-determined number of instances of the same security code 400. Thus, the console 110 is enabled under normal circumstances, but can be disabled after a pre-determined number of repeat uses of the same probe 100.

In the illustrated embodiment, the console 110 is enabled to allow the same probe 100 to be used a second time, but is disabled when an attempt is made to use the same probe a third time. Indeed, the controller 115 may be programmed to allow different numbers of repeat uses of the same probe 100. As a result, a new probe 100 will be required since the same probe 100 can no longer be used with the console 110.

Alternatively, or in addition, the controller 115 can be programmed to generate a visual or audible warning or message to the user that the probe 100 has been used previously (warning can be provided by a display 600 and/or a speaker 610). The controller 115 may also be configured to indicate the number of prior uses of the probe 100.

Figure 7:
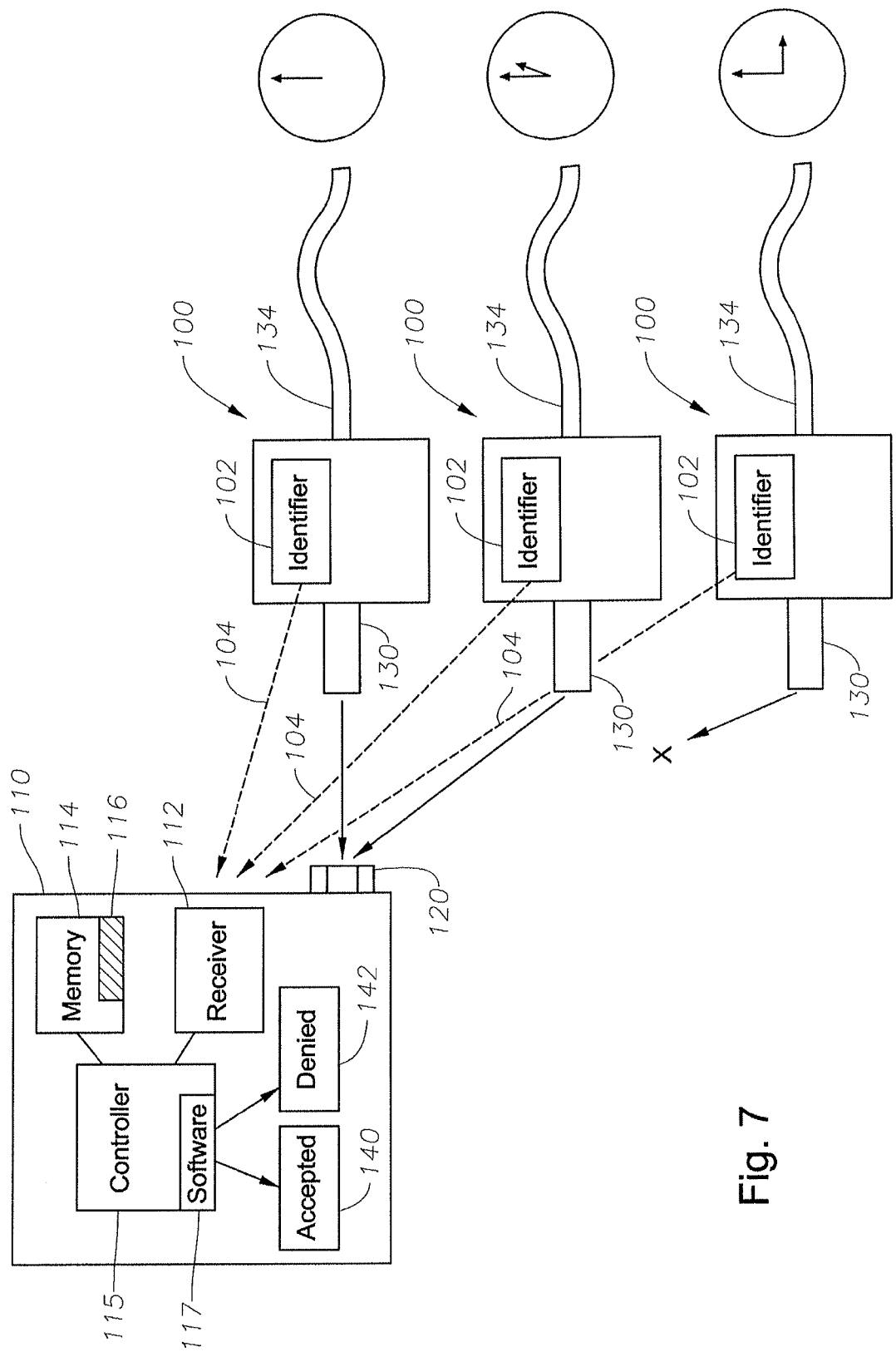
FIG. 7 illustrates a further embodiment in which an ophthalmic surgical device is disabled or conditionally enabled depending on an amount of time that has lapsed since a first or earlier use of the component.

As a further example, referring to FIG. 7, it is possible that the same probe 100 can be used multiple times within a pre-defined period of time. The pre-defined period of time can be, for example, hours, days, weeks, or months. The probe 100 can be used a second or subsequent time if the second or subsequent use occurs during a pre-defined period of time following a prior or previous use of the probe 100.

However, if the probe 100 is used outside of this authorized window, then the controller 115 can disable the console 110, thus requiring a new probe 100. The controller 115 can also be programmed to generate a warning or message as discussed with reference to FIG. 6.

Another example is associating an authorized code with a console 100 and/or component 110 that are manufactured or used in a pre-defined geographic area, country or group of countries. Thus, when the received data satisfies the criteria 116, indicating that the geographic requirements are met, the controller 115 enables the console 110 to be used with the component 100.

In some embodiments, the criteria 116 can be configured to require no security, use, geographic or other enabling data from the component 100 identifier 102 other than identifying data to enable the surgical console 112 to correctly identify the component 100.

Referring to FIG. 8, according to another embodiment, the authorized security codes 520 can be serialized 800 so that particular lots or groups 810 of probes 100 can be identified based on the serialized codes. This may be helpful if, for example, there is a recall of a group of probes 100. The probes 100 that must be recalled can be quickly identified using the serialized security code data 800 and defined lots or groups 810 of probes.

In a further embodiment, referring to FIG. 9, the RFID tag 102 can include the identification data 300 and security data 400, as discussed above, and, in addition, calibration data 900, which is necessary to calibrate the console 110 to work with a particular probe 100 or component. For example, calibration data 900 may be instructions or parameter settings including, for example, laser calibration settings for a particular probe or adaptation. Each probe or adaptation may require the use of a different and unique optical fiber, which changes the optical coupling into the probe or adaptation, and therefore results in a particular calibration.

As a further example, when using a vitrectomy console, calibration data 900 may include instructions or parameter settings relating to laser probe transmissivity, pneumatic vitrectomy probe actuation pressure points, and endoilluminator transmissivity.

Indeed, other calibration may be used depending on the ophthalmic surgical device and component that are utilized. The console 110 can automatically calibrate itself based on the received calibration data 900. Alternatively, the console 110 can be calibrated by a surgeon using the received calibration data 900.

In addition, the identification and/or calibration data may used for various purposes including, for example, enabling or disabling operating parameters that are compatible with the identified component, and invoking certain safety features associated with the identified component. For example, the system may be configured to limit power ranges and/or exposure ranges given a particular type of component. Additionally, the system can be configured to determine whether safety accessories, such as filters, are present so that the identified component can be used without injury to the surgeon. Further, the identification and/or calibration data can be used to generate a user interface that is related to the particular component and presented on a display screen for a surgeon.

Figure 10:
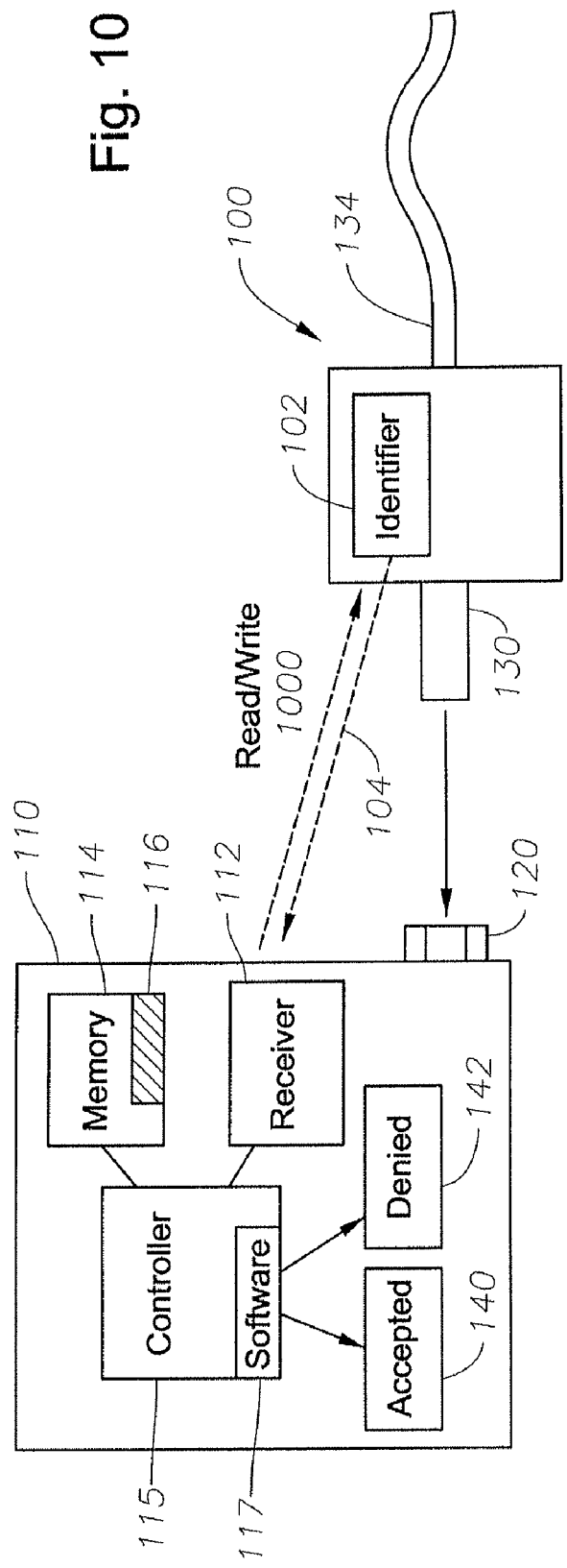
FIG. 10 illustrates another alternative embodiment including read/write applications involving a transceiver in an ophthalmic surgical device and an identifier in a component used with the device.

In a further embodiment, referring to FIG. 10, the RFID readers and tags of the system and component can be configured to two-way or read/write applications 1000. This application may require larger RFID tag 102 data capabilities, e.g., >100 bytes. In this embodiment, the reader (or transceiver) can write different types of data back to the RFID tag 102 for future use or reference. For example, the RFID reader 112 can write information, such as the date of use of a probe 100, a number of times a probe 100 was used, the amount of time the probe 100 was active, the power setting of the probe 100 when active, etc. This information can be particularly useful when the probe 100 is used at a later time, because, for example, a surgeon can review the information and make an assessment regarding the wear and useful life of the probe 100. For example, the useful life of a probe 100 may be decreased when the probe 100 is active for a longer period of time, used at a higher power setting and used multiple times.

Figure 11A:
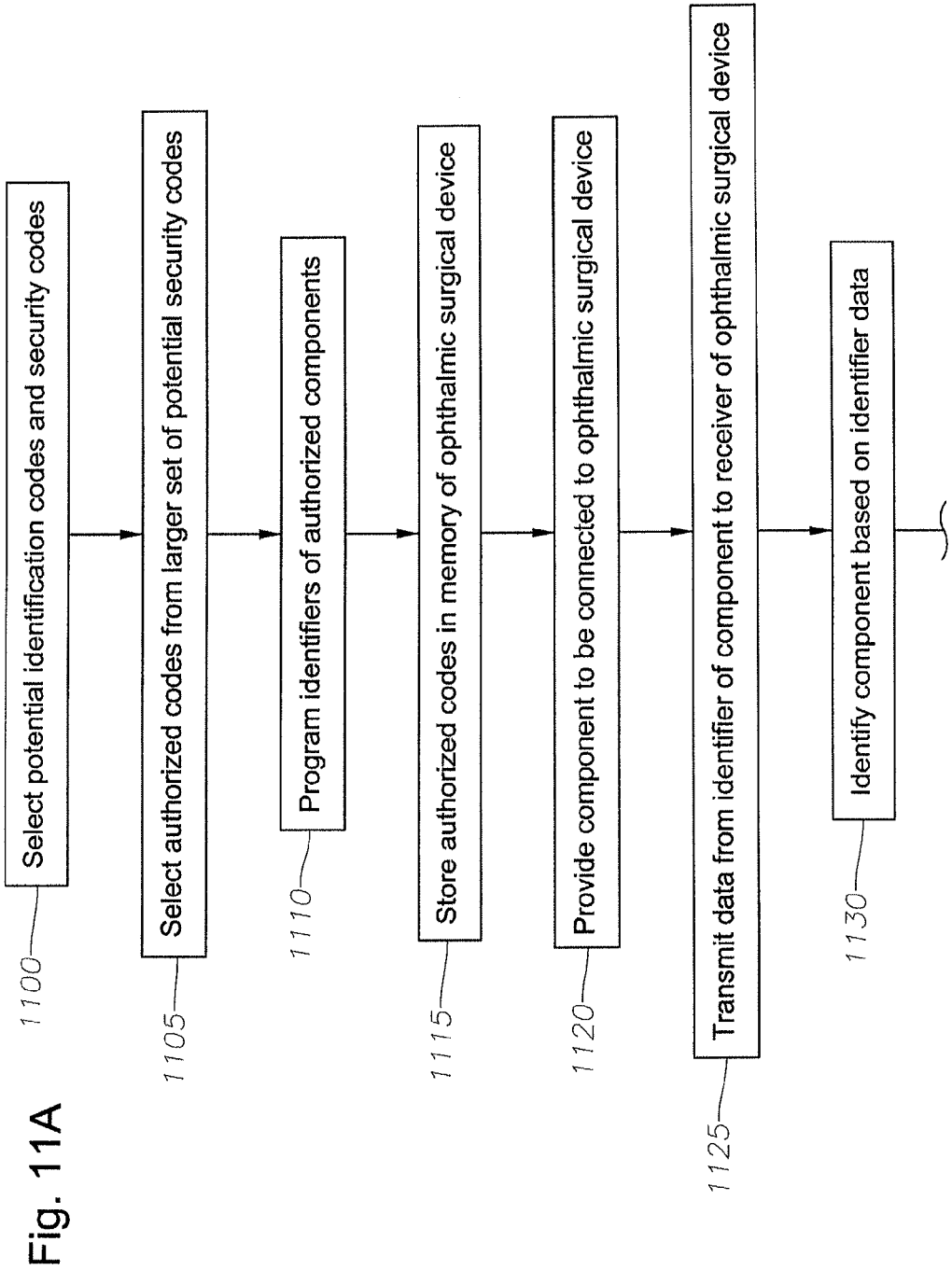
FIGS. 11A-B are flow charts illustrating a manner of identifying components and controlling an ophthalmic surgical device according to various embodiments.
Figure 11B:
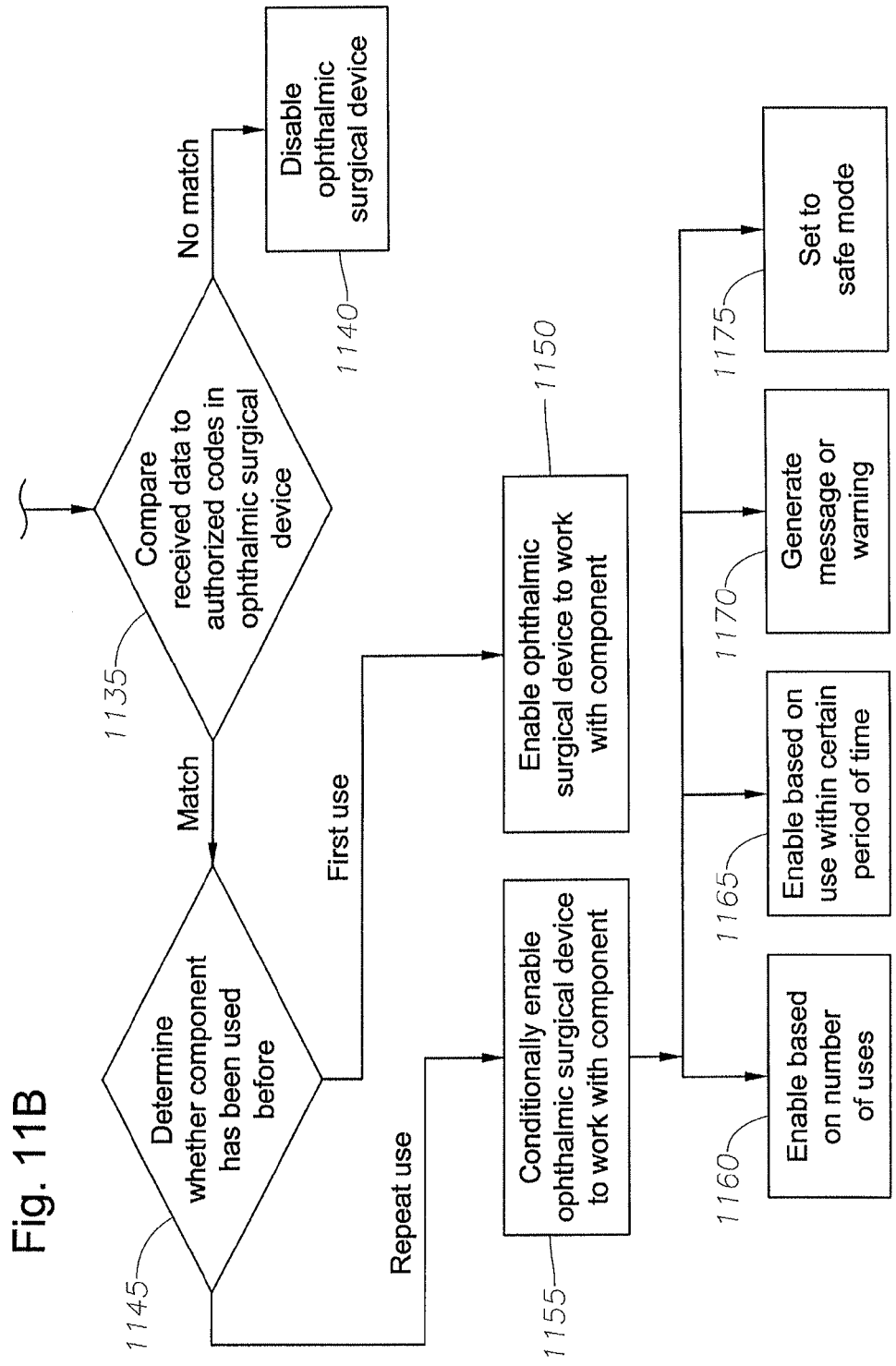

Considering the description of system embodiments, a method for identifying and controlling ophthalmic surgical devices and components is summarized in the flow charts shown in FIGS. 11A-B. Beginning with step 1100, a set of potential identification codes and a set of potential security codes are selected. The potential set of codes includes both authorized and unauthorized codes which will and will not satisfy a set of criteria. In step 1105, a set of authorized codes is selected from the larger set of potential codes. In step 1110, the identifiers or RFID tags of authorized components, e.g., components from original manufacturers, are programmed with one of the authorized codes. In step 1115, if the controller implements criteria based on comparing authorized data to data received from an identifier, the authorized codes are stored in memory of the ophthalmic laser system, such as an ophthalmic laser or vitreoretinal surgical device. If an algorithm is used, the algorithm can be stored in memory without storing authorized data.

In step 1120, a component is provided to be connected to the laser device. In step 1125, data from the RFID tag of the component is transmitted to the receiver or RFID reader in the laser device. The data received from the RFID tag is used to identify the component in step 1130. Data from the RFID device can be used for various purposes including, for example, generating a user interface for presentation on a display screen, enabling or disabling operating parameters that are compatible with the identified component, and invoking certain safety features associated with the identified component. For example, values of certain parameters, such as power and exposure, can be limited to ensure that the device is not operated outside of the specified ranges of operating parameters. Further, the system can be configured to check for safety equipment, such as a filter, that is used with the component.

In step 1135, the data from the RFID tag is processed to determine whether it satisfies certain criteria. In step 1140, the ophthalmic surgical device is disabled if the received data does not satisfy the criteria. In step 1145, the controller determines whether the component has been used before. If the component is being used for the first time, the ophthalmic surgical device can be enabled to work with the component in step 1150. If the component has been used before, in step 1155, the ophthalmic surgical device can be conditionally enabled.

For example, the ophthalmic surgical device can be enabled if the probe has previously been used a certain number of times 1160 or has been previously used within a certain period of time 1165. The controller may also generate a message or warning 1170 for the user to indicate that the probe has been previously used or set the laser device to operate in a safe mode 1175, e.g., at lower power.

Persons skilled in the art will appreciate that there are various modifications that can be made without departing from the scope of embodiments. Embodiments can be used with other types of ophthalmic surgical equipment. Further, embodiments can be used for different purposes, including identification, calibration, compatibility, and lockout purposes. Thus, the illustrative examples set forth above are not intended to be limiting.

Although references have been made in the foregoing description to various embodiments, persons skilled in the art will recognize that insubstantial modifications, alterations, and substitutions can be made to the described embodiments without departing from the invention as claimed in the accompanying claims.

What is claimed:

1. A system for identifying a component for use with a surgical device, comprising:
   a receiver,
   a radio frequency identification (RFID) tag; and
   a controller, wherein;
      the controller and the receiver are operably coupled to the surgical device,
      the RFID tag is attached to the component,
      the RFID tag is operable to transmit stored data to the receiver, the receiver is operable to receive the stored data and provide it to the controller, and the controller is operable to identify the component based on the received stored data and to cause the surgical device to be configured for use with the component; and
      wherein configuring the surgical device for use with the component comprises automatically selecting the component from a group of stored components on the surgical device and enabling use of the selected component with the surgical device.

2. The system of claim 1, wherein the RFID tag transmits the stored data when the component is placed within a surgical workspace.

3. The system of claim 2, wherein the receiver is located within or near to the surgical workspace such that it can receive the stored data transmitted by the RFID tag.

4. The system of claim 1, further comprising a memory, the memory storing criteria, wherein the memory is operably coupled to the controller and wherein the controller determines whether the component can be used with the surgical device based on whether the received stored data satisfies the criteria stored in the memory.

5. The system of claim 4, wherein the criteria is authorized data that is stored in the memory, stored data received from the RFID tag being compared to the authorized data to determine whether the component can be used with the ophthalmic surgical device.

6. The system of claim 4, wherein the criteria is an algorithm, the algorithm being applied to the stored data received from the RFID tag to determine whether the component can be used with the ophthalmic surgical device.

7. The system of claim 1, wherein the surgical device is a vitreoretinal system.

8. The system of claim 7, wherein the component is a vitrectomy handpiece coupled to the vitreoretinal system.

9. The system of claim 8, wherein the vitreoretinal handpiece is a pneumatically or electrically powered scissors that is attached to the vitreoretinal system.

10. The system of claim 7, wherein the component is an endoilluminator probe coupled to the vitreoretinal system.

* * * * *